United States Patent [19]

Fiala

[11] Patent Number: Plant 6,958

[45] Date of Patent: Aug. 1, 1989

[54] CRABAPPLE TREE NAMED SPRING SONG

[75] Inventor: John L. Fiala, Medina, Ohio

[73] Assignee: Chas. Klehm & Son, South Barrington, Ill.

[21] Appl. No.: 213,917

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An ornamental flowering crabapple tree named Spring Song, having a small vase shape, maturing at a height of about 10 feet. The rose buds open to most attractive and delicate billowy light pink blossoms with wide, red-tinged blossom petals. The cultivar is an abundant heavy bloomer, with attractive mint green early spring foliage, burnt-gold autumn fruit and tan-gold bark.

4 Drawing Sheets

1

The present invention comprises a new and distinct cultivar of crabapple tree, botanically known as Malus, and hereinafter referred to by the cultivar name Spring Song.

The new cultivar, discovered by the inventor in 1968, resulted from a controlled cross of seed parent (Malus 'My Bonnie'×Malus zumi) with pollen parent (*Malus dorthea seedling*×*Malus zumi* seedling) in Medina, Ohio.

Asexual reproduction by applicant in Medina, Ohio in the form of rooted cuttings and summer chip budding has demonstrated that the combination of characteristics as herein disclosed for the new cultivar are firmly fixed and are retained through successive generations of asexual reproduction.

Spring Song has not been observed under all possible environmental conditions. The phenotype may vary significantly with variations in environment such as temperature, light intensity, day length, available soil moisture, soil nutrients and pH level.

The following observations, measurements, and comparisons describe trees grown in Klehm Nursery, Barrington, Ill., under conditions which approximate those generally used in commercial practice.

The following traits have been repeatedly observed and are determined to be basic characteristics of Spring Song, which, in combination, distinguish this crabapple tree as a new and distinct cultivar:

1. Spring Song is a relatively small statured, vase shaped tree, about 10′ tall and 5′ wide at maturity.
2. Its deep, rose colored buds open to most attractive and delicate billowy light pink, large blossoms, having red striped, wide blossom petals. The blossoms are often 1.75 to 2 inches wide.
3. It is an annual, heavy bloomer.
4. It produces attractive, mint-green early spring foliage.
5. It produces abundant annual crops of burnt gold autumn fruit.
6. The bark is tan-gold.

Of the many commercial crabapple trees known to the inventor, none is similar enough for meaningful comparison.

The accompanying color photographic drawings show typical characteristics of Spring Song, with colors being as true as possible with illustrations of this type.

2

Sheet 1 is a photograph of Spring Song in perspective view.

Sheet 2 is a closeup photograph of a branch of Spring Song depicting unopen and partially open buds.

Sheet 3 is a closeup photograph of a branch of Spring Song showing buds both closed and in varying states of openness.

Sheet 4 is a color photograph of Spring Song showing berries in full maturity.

In the following description, color references are made to The Royal Horticultural Society Colour Chart (RHS).

TREE

Origin: Seedling.

Parentage:

*Seed parent.*—Malus 'My Bonnie'×*Malus zumi* seedling).

*Pollen parent.*—(*Malus dorthea* seedling×*Malus zumi* seedling).

Classification:

*Botanic.*—Malus×cv Spring Song.

*Commercial.*—Ornamental flowering crabapple.

Propagation: Chip budding, bench grafting or softwood cuttings.

Trunk: Tannish-gold.

Branches: Erect, statuesque.

Height: 10 feet tall and 5′ wide at maturity.

Growth habit: Vase-shaped.

Fruit bearing habit: Annual.

Foliage:

*Size of leaf.*—Medium.

*Shape of leaf.*—Elliptical.

*Margin.*—Entire.

*Color.*—Mint green, approximately 135C.

FLOWERS

Buds:

*Color.*—Deep rose red, approximately 60A–C.

*Size.*—Large.

Size: Large, 1.75″ to 2″ in diameter.

Date of first bloom: Normally May 10–15.

Date of full bloom: Normally May 15–20.

Color: White to light pink mature blossoms with rose red stripes and randomly displayed blotches (approximately 60C–D).

FRUIT

Date of maturity: Approximately October 15.
Shape: Round.
Hardness: Firm.
Color: Burnt gold 17A–B.
Keeping quality: Average.

Insect and disease resistance: Good degree of resistance to both.
Primary use: Landscape and ornamental.

I claim:

1. A new and unique flowering crabapple tree named Spring Song, as illustrated and described.

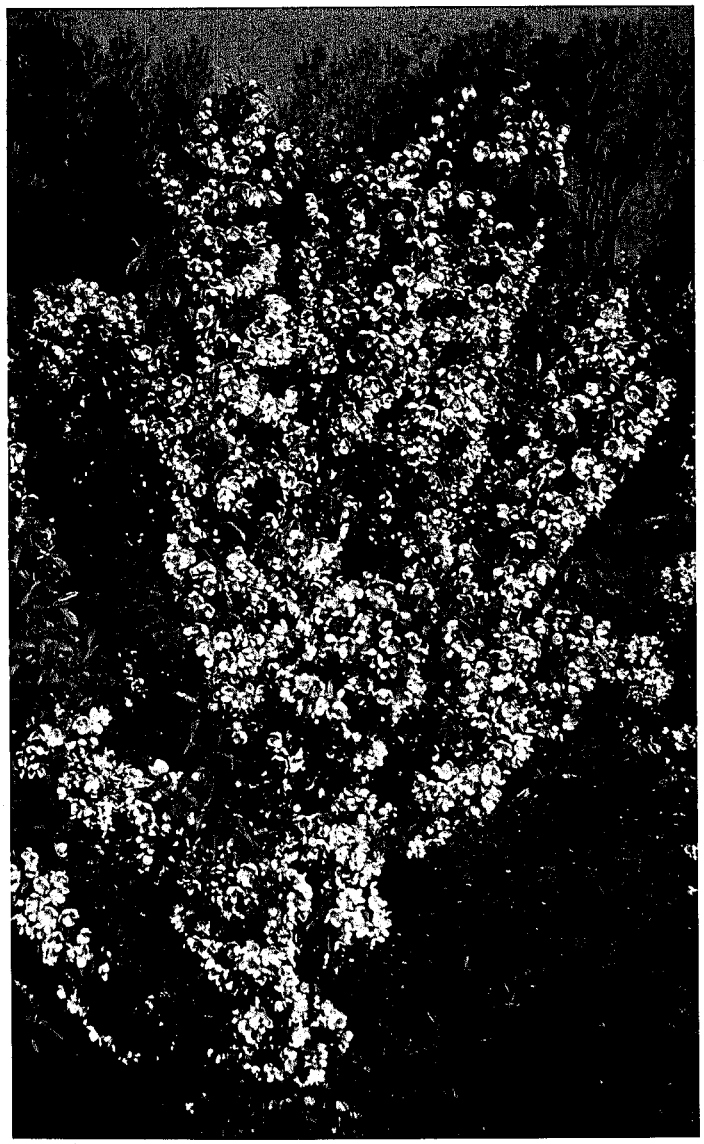

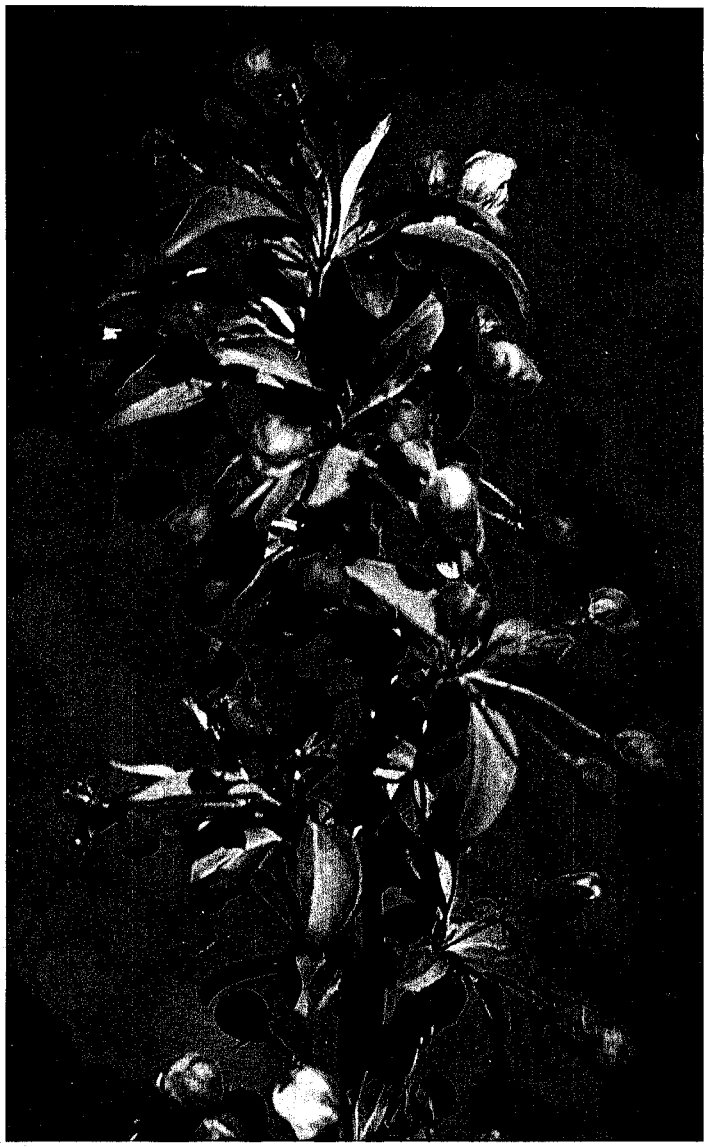

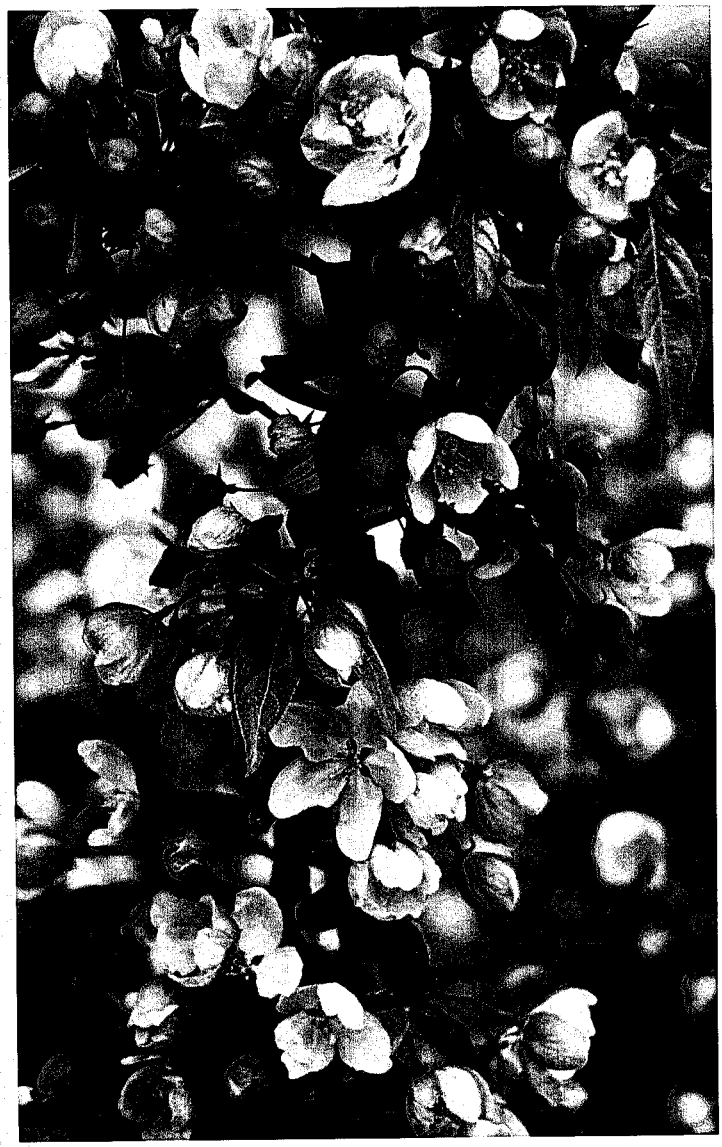

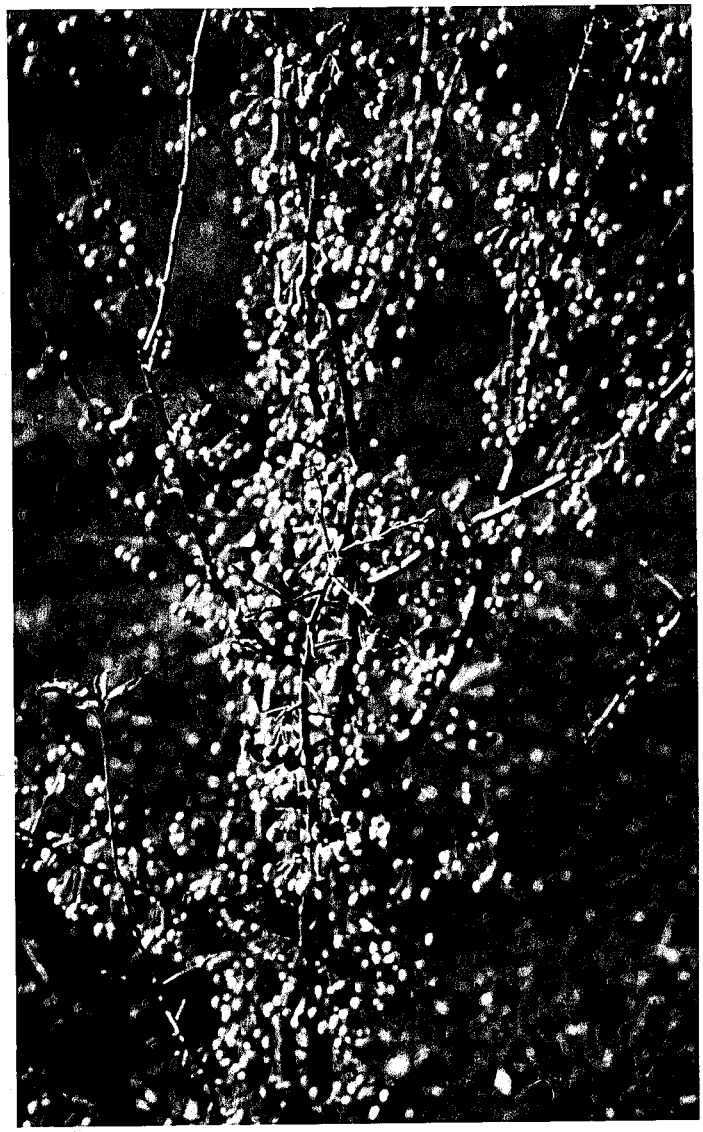

* * * * *